US008722375B2

(12) United States Patent
Costas et al.

(10) Patent No.: US 8,722,375 B2
(45) Date of Patent: May 13, 2014

(54) ALGAL CELL LYSIS AND LIPID EXTRACTION USING ELECTROMAGNETIC RADIATION-EXCITABLE METALLIC NANOPARTICLES

(75) Inventors: Carlos R. Costas, Brandon, FL (US); Christopher R. Eck, Dunedin, FL (US)

(73) Assignee: Raytheon Company, Waltham, MA (US)

( * ) Notice: Subject to any disclaimer, the term of this patent is extended or adjusted under 35 U.S.C. 154(b) by 845 days.

(21) Appl. No.: 12/718,396

(22) Filed: Mar. 5, 2010

(65) Prior Publication Data

US 2011/0217748 A1 Sep. 8, 2011

(51) Int. Cl.
*C12Q 1/68* (2006.01)

(52) U.S. Cl.
USPC ..................... 435/173.7; 435/283.1

(58) Field of Classification Search
CPC ................... C12Q 1/68; C12Q 1/02
USPC ..................... 435/283.1, 289.1, 134
See application file for complete search history.

(56) References Cited

U.S. PATENT DOCUMENTS

| | | | | |
|---|---|---|---|---|
| 5,593,579 | A * | 1/1997 | Reynolds | 210/242.1 |
| 6,514,481 | B1 * | 2/2003 | Prasad et al. | 424/9.32 |
| 6,623,945 | B1 | 9/2003 | Nair et al. | 435/173.4 |
| 7,001,629 | B1 | 2/2006 | Mengal et al. | 426/241 |
| 2004/0181114 | A1 | 9/2004 | Hainfeld et al. | 600/1 |
| 2005/0020869 | A1 | 1/2005 | Hainfeld et al. | 600/1 |
| 2005/0256360 | A1 | 11/2005 | Hainfeld et al. | 600/1 |
| 2006/0190063 | A1 | 8/2006 | Kanzius | 607/101 |
| 2008/0090284 | A1 * | 4/2008 | Hazlebeck et al. | 435/259 |
| 2008/0160653 | A1 | 7/2008 | Park et al. | 438/14 |
| 2008/0171366 | A1 * | 7/2008 | Cheong et al. | 435/91.2 |
| 2009/0029445 | A1 | 1/2009 | Eckelberry et al. | 435/257.1 |
| 2009/0071064 | A1 * | 3/2009 | Machacek et al. | 44/308 |
| 2009/0186060 | A1 | 7/2009 | Hainfeld et al. | 424/422 |

FOREIGN PATENT DOCUMENTS

| | | | | |
|---|---|---|---|---|
| JP | 62087060 | | 4/1987 | A23K 1/18 |
| WO | WO 01/19963 | | 3/2001 | C12N 5/00 |
| WO | 2009/126571 | | 10/2009 | A61B 18/18 |

OTHER PUBLICATIONS

Lee SJ et al., Letters in Applied Microbiology, vol. 27, p. 14-18, 1998.*
Bakandritsos et al., Langmuir, vol. 24, No. 20, p. 11489-11496, 2008.*
Lee et al., Letters in Applied Microbiology, vol. 27, p. 14-18, 1998.*
Safarik et al., Monatshefte fur Chemie, vol. 133, p. 737-759, 2002.*
Torres de Araujo et al., Biophysical Journal, vol. 50, No. 2, p. 375-378, 1986.*
International Search Report and Written Opinion; PCT/US2011/024820; pp. 8, Apr. 20, 2011.
Wei Lu; "Effect of Electric Field on Exfoliation of Nanoplates"; Applied Physics Letters, vol. 89; pp. 3, 2006.
Boldor et al.; "Design and Implementation of a Continuous Microwave Heating System for Ballast Water Treatment"; Environ. Sci. Technol., vol. 42; pp. 4121-4127, 2008.
Goldstein et al.; "Convective Heat Transport in Nanofluids"; University of Minnesota; pp. 16, Sep. 2000.

* cited by examiner

*Primary Examiner* — Susan Hanley
*Assistant Examiner* — Damon B Bowe
(74) *Attorney, Agent, or Firm* — Lando & Anastasi, LLP

(57) ABSTRACT

According to one embodiment, the disclosure provides a system for algal cell lysis. The system may include at least one algal cell, a plurality of metal nanoparticles, and an electromagnetic radiation generator. The generator may be able to generate radio frequency or microwave radiation that excites the plurality of metal nanoparticles, resulting in lysis of the algal cell. The disclosure also provides a system for recovery of a lipid from an algal cell similar to the above system but also including a separator. The disclosure further provides a method of recovering a lipid from an algal cell by supplying a plurality of metal nanoparticles to at least one algal cell, exciting the plurality of metal nanoparticles with radio frequency or microwave electromagnetic radiation, lysing the algal cell to release the lipid, and separating the lipid from the lysed algal cell.

14 Claims, 3 Drawing Sheets

ALGAL CELL LYSIS AND LIPID EXTRACTION USING ELECTROMAGNETIC RADIATION-EXCITABLE METALLIC NANOPARTICLES

TECHNICAL FIELD

The current disclosure relates to systems and methods of extracting lipids from algae by providing metallic nanoparticles to the algae cells then exciting the nanoparticles using electromagnetic radiation, particularly radio frequency (RF) or microwave radiation. These lipids may then be further processed to produce useful products, such as plastics, jet fuel, cosmetics, and biodiesel.

BACKGROUND OF THE DISCLOSURE

Algae are simple, single-celled plants that can inherently produce lipids and other materials that can be processed to create biofuels, plastics and other materials traditionally derived from petrochemicals. Algae produce these valuable materials using nothing more than sunlight, carbon dioxide, fresh or salt water, and trace amounts of nutrients. Further, production of biofuels from algae results in few unwanted waste products. Accordingly, algae are a major potential source of renewable energy and petrochemical replacement materials.

One problem with the use of algae as a renewable energy and materials source has been the extraction of lipids or other useful materials from the algae. Algae have a durable cell wall that must be disrupted in order to effectively obtain the useful materials inside the cell. Various methods have been tried, but all suffer from deficiencies. For example, sonication methods use sound waves to break open algal cells, but is expensive and inefficient. Mechanical pressure may be used to burst algal cells, but is also expensive and difficult to scale up for bulk processing. Electroporation uses high powered electric fields to break cells open, but is very energy intensive and costly. Enzymatic extraction uses enzymes to break down algal cell walls in a highly efficient manner, but is extremely expensive and results in contamination of the resulting biomass. Finally, centrifuge-based methods, including one method using small ceramic balls, may also be used to burst algal cell walls, but these techniques are unproven at a large scale and involve large equipment and uncertainties in process parameters, such as flow rates.

Accordingly, there is a need for other methods and systems for disrupting the algal cell walls while leaving the useful materials from the algae substantially in a useful form.

SUMMARY OF THE DISCLOSURE

The current invention provides methods and systems for disrupting the algal cell walls while leaving the useful materials from the algae substantially in a useful form.

According to one embodiment, the disclosure provides a system for algal cell lysis. The system may include at least one algal cell, a plurality of metal nanoparticles, and an electromagnetic radiation generator. The generator may be able to generate radio frequency or microwave radiation that excites the plurality of metal nanoparticles, resulting in lysis of the algal cell.

According to more specific embodiments, the algal cell may include a lipid that is released when the cell is lysed. According to other specific embodiments, the metal nanoparticles may be inside, outside of the cell, on or in the cell wall, or in some combination of these areas prior to lysis. According to more specific embodiments, the metal nanoparticles may experience ionic conduction or dipolar reorientation in response to the electromagnetic radiation, or they may be ferromagnetic. According to one additional specific embodiment, the metal nanoparticles may not be coated or modified in order to increase uptake by the algal cells. According to a more specific embodiment, the system may also include an agent to increase uptake of the metal nanoparticles by the algal cells. According to still another embodiment, the nanoparticles may be coated or modified to increase uptake by the algal cells.

According to a second embodiment the disclosure provides a system for recovery of a lipid from an algal cell. The system may include at least one algal cell, a plurality of metal nanoparticles, an electromagnetic radiation generator, and a separator. The generator may be able to generate radio frequency or microwave radiation that excites the plurality of metal nanoparticles, resulting in lysis of the algal cell.

According to more specific embodiments, the metal nanoparticles may be may be inside, outside of the cell, on or in the cell well, or in some combination of these areas prior to lysis. According to more specific embodiments, the metal nanoparticles may experience ionic conduction or dipolar reorientation in response to the electromagnetic radiation, or they may be ferromagnetic. According to another additional specific embodiment, the metal nanoparticles may not be coated or modified in order to increase uptake by the algal cells. According to a more specific embodiment, the system may also include an agent to increase uptake of the metal nanoparticles by the algal cells. According to still another embodiment, the nanoparticles may be coated or modified to increase uptake by the algal cells. According to further specific embodiments, the separator may include a centrifuge, a skimmer, or a flocculation recovery device.

According to a third embodiment, the disclosure provides a method of recovering a lipid from an algal cell by supplying a plurality of metal nanoparticles to at least one algal cell. The plurality of nanoparticles may be located inside or outside the algal cell, in or on a cell wall of the algal cell, or in a combination of these locations. The method also includes exciting the plurality of metal nanoparticles with radio frequency or microwave electromagnetic radiation, lysing the algal cell to release the lipid, and separating the lipid from the lysed algal cell.

According to a more specific embodiment, supplying may include allowing the algal cells to take up the metal nanoparticles. According to other specific embodiments, exciting may include inducing ionic currents in the metal nanoparticles, inducing dipolar reorientation of the metal nanoparticles, or inducing a ferromagnetic effect in the metal nanoparticles. According to still further specific embodiments, separating may include skimming the lipid from the lysed algal cell, flocculation, or centrifugation.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

The current disclosure relates to a system and method for lysing algal cells using metal nanoparticles and electromagnetic radiation. According to one embodiment, the algal cells contain lipids, including lipid oils, that are released and that may be further processed into useful materials such as biofuels or plastics.

Figure 1:
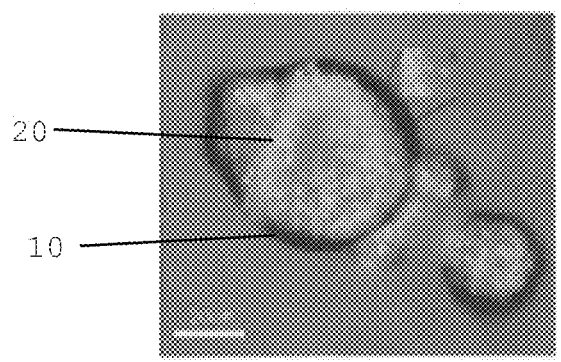
FIG. 1 shows metal nanoparticles incorporated in algae, according to an embodiment of the current disclosure.
Figure 2A:
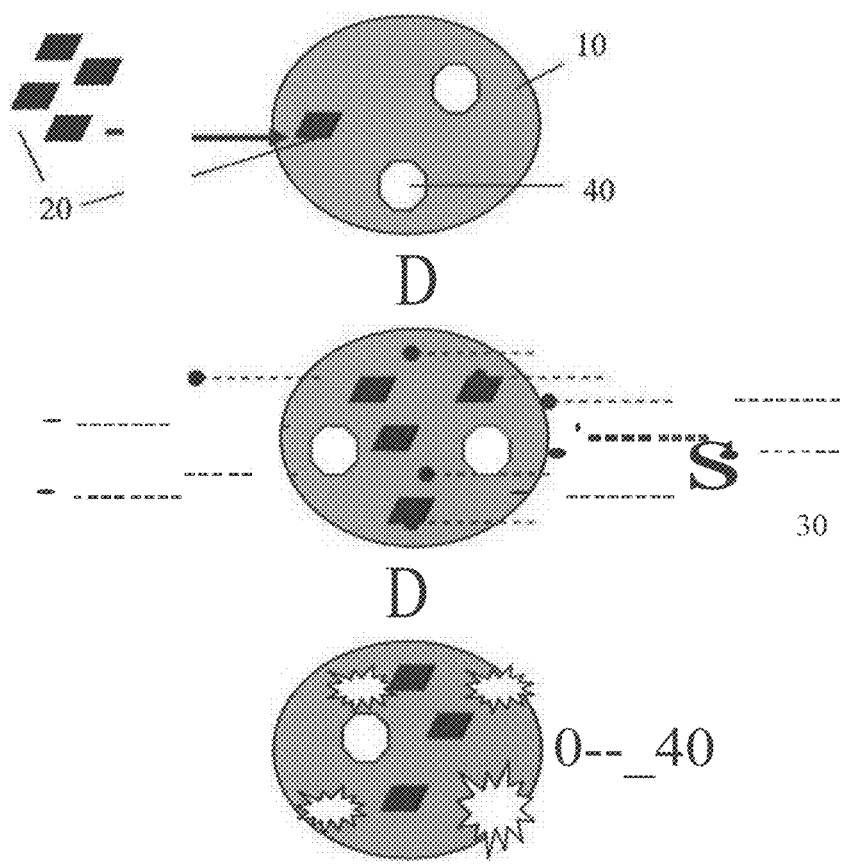
FIG. 2 illustrates lysing algal cells using metal nanoparticles located within the cells (FIG. 2A) or outside of the cells (FIG. 2B), according to embodiments of the current disclosure.
Figure 2B:
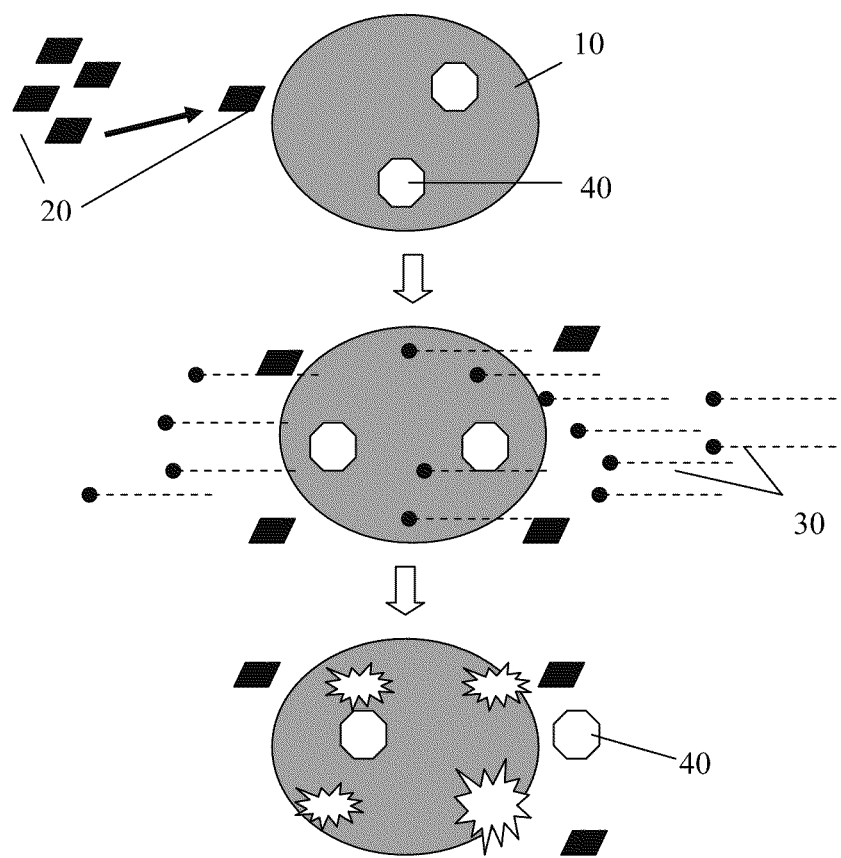

According the embodiment shown in FIGS. 1 and 2, algae cells 10, may be provided with nanoparticles 20. The nanoparticles 20 may be inside the algae cells 10 (as shown in FIGS. 1 and 2A) or outside the algae cells (as shown in FIG. 2B), or both inside and outside the algal cells (not shown), or on or in the algal call walls (not shown).

The algae cells may be any type of algae cell suitable for production of useful materials, such as lipids, that may be processed into other materials such as biofuels and plastics. For example, the algae may be fresh water or salt water algae. They may also be cyanobacteria algae or diatom algae. Although microalgae, which tend to be present in single cells, are currently more prevalent in biofuel production, certain macroalgaes, in which cells clump and form larger structures may also be used. In particular embodiments, the algae may be engineered algae, such as algae containing recombinant genes. Specific strains of algae that may be used include *Schiochytrium, Neochloris oleoabundans, Crypthecodinium cohnii, Thalassiosira pseudonana, Tetraselmis suecica, Stichococcus, Scenedesmus* TR-84, *Phaeodactylum tricornutum, Nitzschia* TR, *Nannochloropsis, Nannochloris, Hantzschia* DI, *Dunaliella tertiolecta, Cyclotella* DI, *Ankistrodesmus* TR-87, *Botryococcus braunii, Pleurochrysis camerae* (CCMP647), a *Dunaliella* strain such as *Dunaliella salina* or *Dunaliella tertiolecta*, a *Chlorella* strain such as *Chlorella Vulgaris, Chlorella* sp. 29, or *Chlorella Protothecoides*, a *Gracilaria* strain, or *Sargassum*, or engineered variants thereof. According to one embodiment, the algae may be a monoculture of substantially one algae strain. According to another embodiment, the algae may include more than one algae strain.

The metal nanoparticles may include any type excitable by electromagnetic radiation 30. According to a particular embodiment, they may be excitable by radio frequency (RF) radiation, which typically has a frequency of between 3 kHz and 300 MHz. According to another embodiment, they maybe excitable by microwave radiation, which typically has a frequency between 300 MHz and 300 GHz. According to one particular embodiment, the electromagnetic radiation may have a frequency of between 885 MHz and 945 MHz, more particularly around 915 MHz. According to another particular embodiment, the electromagnetic radiation may have a frequency of between 2420 and 2480 MHz, more particularly 2450 MHZ. The overall energy of the electromagnetic radiation may be varied. Further, the electromagnetic radiation may be delivered in a pulsed or continuous wave (cw) manner. In general, the parameters, such as the energy or duration, of the electromagnetic radiation may be arranged so that less energy is supplied to the algal cells than would be needed to cause cell lysis if no metal nanoparticles were present. Typically low power microwaves or RF waves at typical industrial or commercial frequencies may be used, which may result in lower costs. The particular frequency, wavelength, power, energy and other parameters may vary depending on the particular metal nanoparticles used. For example, some particles may have resonance frequencies at which they are very rapidly heated. In particular embodiments, the electromagnetic radiation may exhibit a uniform energy distribution, which may increase yield or efficiency of lipid recovery from the algal cells.

The metal nanoparticles may be of any size in the range of 1 nm to 999 nm. Nanoparticle size characterization may be according to the National Institute of Standards and Technology Special Publication 960-1 (January, 2001). According to particular embodiments, the metal nanoparticles may be less than 50 nm, less than 100 nm, less than 200 nm, less than 300 nm, less than 400 nm, less than 500 nm, less than 600 nm, less than 700 nm, less than 800 nm, less than 900 nm, or less than 999 nm in size. According to other particular embodiments, the nanoparticles may also be greater than 1 nm, greater than 50 nm, greater than 100 nm, greater than 200 nm, greater than 300 nm, greater than 400 nm, greater than 500 nm, greater than 600 nm, greater than 700 nm, greater than 800 nm, or greater than 900 nm in size. According to still other embodiments, the nanoparticle sizes may be in ranges between any of the values in the preceding two embodiments. For example, the nanoparticle sizes may be between 200 and 600 nm. Nanoparticle size may be selected based on a variety of factors including inducing or avoiding uptake by algal cells, ability to mechanically disrupt the cell wall, ability to dissipate heat, and ease of removal of material from lysed algal cells. In general, smaller nanoparticles may be taken up more easily by algal cells, while larger nanoparticles may have tendency to remain outside of the cells in the culture medium.

According to one embodiment, the metal nanoparticles may be solid. According to another embodiment, they may be hollow. According to a particular embodiment, metal nanoparticles may have a shell and core design. Metal nanoparticles may have any shape. Particular shapes, such as non-round shapes, may be more suited to mechanical disruption of cells walls. Certain shapes may also prove more or less amendable to uptake by algal cells. Shape may further influence the ease of applying and effectiveness of nanoparticle coatings, if any are present.

Algae naturally take up metal particles and this ability may be exploited by one embodiment in which the metal nanoparticles are not coated or modified in order to increase uptake. In this embodiment, uptake relies on the interaction of algal metal uptake mechanisms and the metal of the nanoparticles. According to another embodiment, the metal nanoparticles may be coated to decrease or prevent their uptake by algal cells. According to a third embodiment, the metal nanoparticles may be coated with a material to increase their uptake by algal cells. According to a fourth embodiment, the metal nanoparticles may be administered to the algal cells in combination with a non-coating additive that increases their uptake by the algal cells. According to a fifth embodiment, the metal nanoparticles may be administered to the algal cells in combination with a non-coating additive that decreases or prevents their uptake by algal cells.

In some embodiments, non-coated nanoparticles may be preferred due to simplicity of manufacture and decreased cost. Simple administration of nanoparticles with a non-coating additive may also provide greater simplicity and lower cost as compared to coated nanoparticles.

According to another embodiment, nanoparticles may be actively introduced into the algal cells. For example, they may be propelled at a speed sufficient to allow them to enter the cells. According to a specific embodiment, a system similar to current systems used to introduce nucleic acids into plant cells may be used. In particular, the system may be similar to a "gene gun" or a "bioballistic device." In one embodiment of such systems, non-coated metal nanoparticles may be used.

According to one embodiment, the metal nanoparticles may have a high dielectric constant. Electromagnetic radiation may induce ionic conduction in this type of nanoparticle. Inductive heating may occur, for example via Eddy or Foucalt currents. In general, metallic nanoparticles conduct heat much better than aqueous solutions, such as the algae culture medium. Larger nanoparticles may conduct heat by advection as well as by becoming heated themselves.

According to another embodiment, the metal nanoparticles may be dipolar. When exposed to electromagnetic radiation these nanoparticles tend to undergo dipolar reorientation. In this process polarized nanoparticles attempt to align themselves in phase with the electric/magnetic field. Typically that field is changing due to movement of the fluid in which the algae are located. As a result, the particles also move and collide with one another, increasing their kinetic energy. These mechanisms generate heat via friction. Also, particularly if the nanoparticles are located in algal cells, collisions may also mechanically disrupt the algal cell wall. Under certain conditions the nanoparticles may also begin to travel at very high speeds in the water medium inside or around the algal cells, which may also lead to cell wall disruption.

According to a third embodiment, the metal nanoparticles may be ferromagnetic. These particles may exhibit a ferromagnetic effect that is similar to the dipolar effect described above. Ferromagnetic effects may cause algal cell wall disruption even more rapidly or in the presence of even less electromagnetic radiation because ferromagnetic material reacts instantaneously to changes in electric/magnetic fields.

Metal nanoparticles according to some embodiments of the current disclosure may contain at least some metal or metal compound, such as metal oxide. According to particular embodiments, the metal nanoparticles may contain by weight or molar ratio at least 50% metal, at least 60% metal, at least 70% metal, at least 80% metal, at least 90% metal, at least 95% metal, or at least 99% metal. Particularly if not present in a metal compound, non-metal elements may interfere with the ability of the metal nanoparticles to be excited by electromagnetic radiation. Metal nanoparticles may contain substantially only one metal or metal compound, or combinations of more than one metal or metal compound. According to one embodiment, the metal nanoparticles may include metal that are substantially non-toxic or which may be removed from the lipids released by algal cells to substantially non-toxic levels. Cheaper metals may also be preferred.

Specific metal nanoparticles that may be used in embodiments of the disclosure include gold, silver, copper, tin, tantalum, vanadium, molybdenum, tungsten, osmium, iridium, rhenium, hafnium, thallium, lead, bismuth, gadolinium, dysprosium, manganese, holmium, uranium, cobalt, platinum, palladium, iron, titanium, zinc, and oxides, hydroxides, and salts thereof, silver silicide, gallium selenide, indium selenide, cadmium selenide, cadmium sulfide, indium arsenide, and indium phosphide. According to one embodiment, gold or other metal nanoparticles may be formed by reducing a gold or other metal ion with a reducing agent. Suitable reducing agents include phosphorus, borane, citrate, sodium borohydride, ionizing radiation, alcohols, and aldehydes. Non-metal elements that may be included in the nanoparticles include silicon, oxygen, phosphorus and carbon.

Nanoparticles may be located inside or outside of the algal cells. They may also be located on or in the algal cell wall. In some embodiments, nanoparticles may be substantially concentrated in one area, such as outside the algal cells. In other embodiments, nanoparticles may be located in any combination of inside or outside of the algal cells, or in or on the algal cell wall. Inside the algal cells, the nanoparticles may be located in various locations, such as in the cytoplasm or in vacuoles or other membrane-bound internal structures, or both.

The concentration of the nanoparticles in the algal cells and/or in the liquid medium surrounding the algal cells may vary depending on the type of nanoparticle and electromagnetic radiation used. Typically there will be a trade-off between the concentration of nanoparticles and the amount of electromagnetic energy needed to cause lysis of the algal cells. According to one embodiment, the concentration of the nanoparticles is such that they cause a statistically significant decrease in the amount of electromagnetic energy needed for cell lysis as compared to a sample where cells are lysed only with electromagnetic energy and without any nanoparticles. Due to a likely increased ability of metal nanoparticles to cause cell lysis when the nanoparticles are inside algal cells, the concentration of metal nanoparticles may be less in embodiments in which the nanoparticles are taken up by the algal cells.

After lysis, lipids, which may be in the form of lipid oils 40, are released from the algal cells through the disrupted cell walls. The lipids may be any type produced by the algae. For example, they may be triacylglycerols. The lipids may be free in the algal cells, but are often contained in intracellular compartments, such as vacuoles. Upon lysis of the cell wall, the lipids may remain in these storage compartments and may be released from the cell in the storage compartments. In another embodiment, the storage compartments may also be lysed, such that lipids are released from the cell free of storage compartments. In another embodiment, lipids may be released both inside storage compartments and free of storage compartments. Lysis conditions, such a type and concentration of nanoparticles and type and parameters or electromagnetic radiation may affect whether storage compartments are also lysed. Typically, storage compartments will be more readily lysed in embodiments in which the algal cells take up the nanoparticles than in embodiments in which the nanoparticles remain substantially outside of the algal cells.

Figure 3:
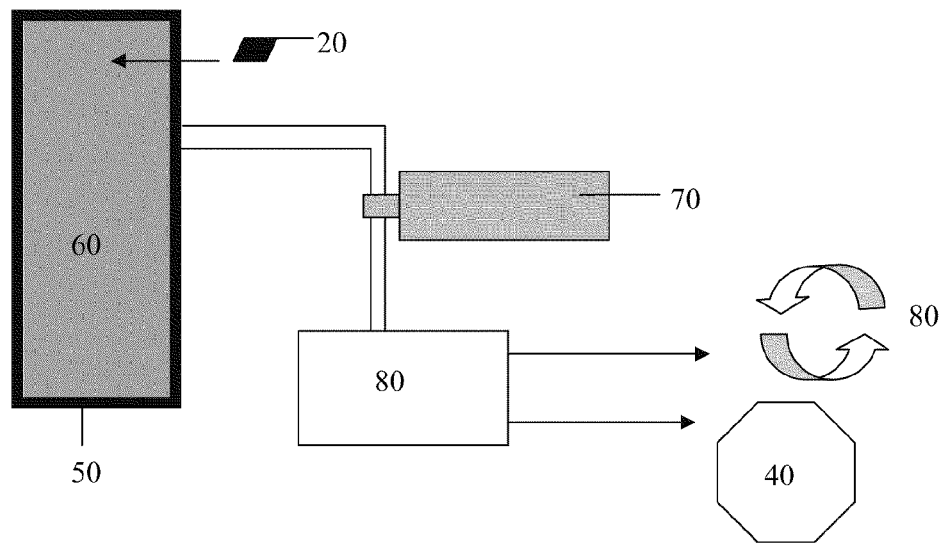
FIG. 3 illustrates a system for producing lipids from algae, according to an embodiment of the current disclosure.

As shown in the embodiment in FIG. 3, algal cells 10 are grown in bioreactor 50. Bioreactor 50 may be an industrial bioreactor, such as a photobioreactor, an open pond, or a hybrid reactor, such as a combined pond and bioreactor system. Nanoparticles 20 are added to bioreactor 50. After addition of nanoparticles, algae culture 60 containing algae cells 10 is removed from bioreactor 50. Algae culture 60 may be processed or treated. For example, some water may be removed via filtering, centrifugation, froth flotation, flocculation, combination of these processes, or other processes. Removal of algae culture 60 and removal of water may precede the addition of nanoparticles in some embodiments. In such embodiments, algae culture 60 may be stored in a separate container (not shown) for addition of nanoparticles 20. This provides the advantage of keeping nanoparticles separate from the normal bioreactor 50. In other embodiments, nanoparticles 20 may be present in bioreactor 50 for all or a substantial part of the growth phase of the algae.

According to one embodiment (not shown) the system may include a device for propelling metal nanoparticles into the algal cells, such as gene gun or other bioballistic device. The effect of such a device may be equivalent to algal cells taking up nanoparticles, i.e., the nanoparticles become present in the inside of the cells.

After, algae culture 60 has taken up nanoparticles 20 or they are present in the surrounding medium, it is then subjected to electromagnetic radiation via generator 70. In one embodiment, algae culture 60 may flow through a cavity in generator 70. In other embodiments, algae culture 60 may be subject to irradiation in a generally stationary manner, such as while in a container (not shown).

After sufficient irradiation with electromagnetic radiation to lyse a substantial fraction of the cell walls of algae cells 10 in algae culture 60, algae culture 60 may be further processed in separator 90 to remove lipids. For example centrifugation, flocculation, skimming and combinations of these methods or other methods may be used to separate lipid oil 40 from residual biomass 80. Nanoparticles 20 may be present in lipid oil 40, residual biomass 80, or both. Nanoparticles 20 may also be present in waste water derived from the overall process. Nanoparticles 20 may be recovered using any suitable technique, such as magnetic attraction, centrifugal separation, or chemical separation. According to some embodiments, nanoparticles 20 may be reused. Residual biomass 80 and any waste water may also be reused in the process, for example as nutrient supplies for growing algae cultures or, if some algal cells survive, as a starter sample for a new algae culture.

According to one embodiment, the system of FIG. 3 may be operated as a closed loop system, with nanoparticles 20, residual biomass 80, and water returning to bioreactor 50 after removal of lipid oil 40.

Generator 70 may be an industrial microwave or RF generator. It may contain a tuned cavity through which algal culture 60 passes. The generator may also contain additional components such as a wave guide, a tuning coupler, and a power coupler (not shown). In some systems, the flow of algae culture 60 through the generator 70 may be continuous or continuous for a batch time.

Figure 4:
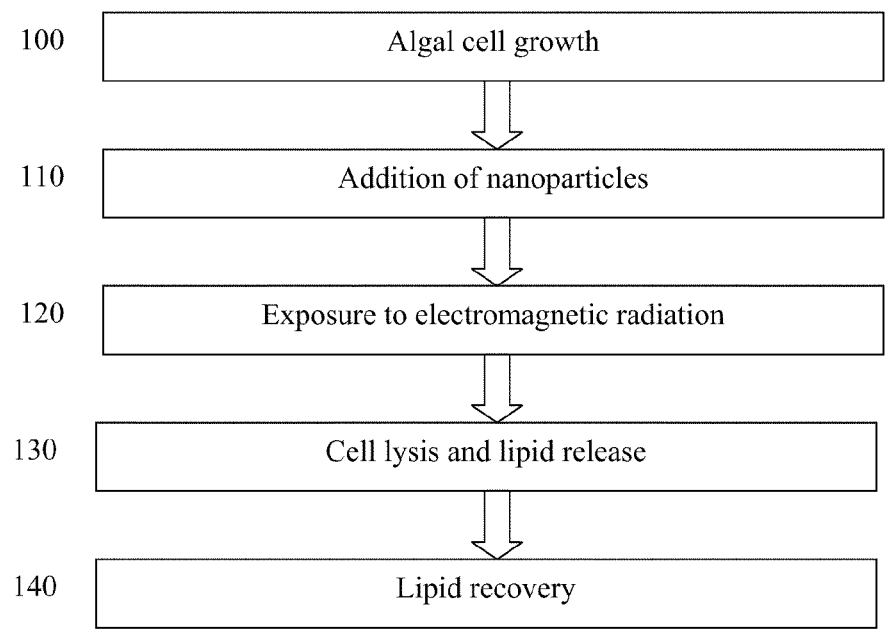
FIG. 4 illustrates a method for producing lipids from algae, according to an embodiment of the current disclosure.

According to the embodiment shown in FIG. 4, a method of lysing algae to obtain lipids contain therein is provided. The method may use portions of any of the systems described above. In step 100, algal cells are grown until they contain a suitable amount of lipids. In step 110, metal nanoparticles are added to the algae. These nanoparticles may be present during growth step 100. The nanoparticles may be taken up by the algae cells or they may simply remain in the medium or both. In step 120, the algae cells are subjected to electromagnetic radiation that excites the metal nanoparticles. In particular embodiments the electromagnetic radiation may be RF or microwave radiation. In step 130, cell lysis occurs as the cell wall of the algae cells is disrupted and lipids are released. In step 140, lipids from the algae cells are recovered.

Lipids obtained using the systems and methods of the current disclosure may be further processed to produce useful materials. For example, triacylglycerols may be cleaved into components by transesterification. The transesterification products may be used to produce biodiesel. Algal lipids may also be used in the production of biobutanol, biogasoline, methane, straight vegetable oil, jet fuel, plastics and even cosmetics.

Although only exemplary embodiments of the invention are specifically described above, it will be appreciated that modifications and variations of these examples are possible without departing from the spirit and intended scope of the invention. For example, in the specification particular measurements are given. It would be understood by one of ordinary skill in the art that in many instances other values similar to, but not exactly the same as the given measurements may be equivalent and may also be encompassed by the present invention. Further, although the above description focuses on recovery of lipids from algae, other materials, such a proteins and carbohydrates, may also be released from algal cells or become more accessible after cell lysis. If useful, these materials may also be separated and processed. For example, algal cells engineered to produce particular proteins may be lysed using the nanoparticle methods of this disclosure. Recovery methods may vary depending on the material recovered.

The invention claimed is:

1. A system for recovery of a lipid from an algal cell comprising:
    a bioreactor comprising at least one algal cell comprising a lipid;
    a plurality of metal nanoparticles;
    an electromagnetic radiation generator, wherein the generator is operable to generate radio frequency or microwave radiation that excites the plurality of metal nanoparticles, resulting in lysis of the algal cell and release of the lipid from the lysed algal cell;
    a separator connected downstream of the bioreactor and operable to separate the lipid from the lysed algal cell and remove the lipid by way of a first outlet of the separator; and
    a recycle stream connected to a second outlet of the separator and configured to return at least one of nanoparticles, a residual biomass and water to the bioreactor.

2. The system of claim 1, wherein the plurality of the metal nanoparticles are located inside of the algal cell prior to lysis.

3. The system of claim 1, wherein the plurality of metal nanoparticles are located outside of the algal cell prior to lysis.

4. The system of claim 1, wherein the plurality of metal nanoparticles are located both inside and outside of the algal cell prior to lysis.

5. The system of claim 1, wherein the plurality of metal nanoparticles are located on or in a cell wall of the algal cell prior to lysis.

6. The system of claim 1, wherein the plurality of metal nanoparticles are located both inside and outside of the algal cell, both inside the algal cell and on or in the cell wall, both outside the algal cell and on or in the cell wall, or inside and outside of the algal cell and on or in the cell wall prior to lysis.

7. The system of claim 1, wherein the metal nanoparticles are operable to experience ionic conduction when excited by the electromagnetic radiation.

8. The system of claim 1, wherein the metal nanoparticles are operable to experience dipolar reorientation when excited by the electromagnetic radiation.

9. The system of claim 1, wherein the metal nanoparticles comprise a ferromagnetic material.

10. The system of claim 1, wherein the system further comprises an agent to increase uptake of the metal nanoparticles by the algal cells.

11. The system of claim 1, wherein the metal nanoparticles are coated or modified to increase uptake by the algal cells.

12. The system of claim 1, wherein the separator comprises a centrifuge.

13. The system of claim 1, wherein the separator comprises a skimmer.

14. The system of claim 1, wherein the separator includes a flocculation recovery device.

* * * * *